United States Patent
Panunzio et al.

(10) Patent No.: US 7,858,778 B2
(45) Date of Patent: *Dec. 28, 2010

(54) PROCESS FOR THE PREPARATION OF 10,11-DIHYDRO-10-HYDROXY-5H-DIBENZ [B,F]AZEPINE-5-CARBOXYAMIDE

(75) Inventors: Mauro Panunzio, Treviglio (IT); Eileen Campana, Treviglio (IT); Gabriele Breviglieri, Treviglio (IT)

(73) Assignee: Farchemia S.R.L., Treviglio (IT)

( * ) Notice: Subject to any disclaimer, the term of this patent is extended or adjusted under 35 U.S.C. 154(b) by 735 days.

This patent is subject to a terminal disclaimer.

(21) Appl. No.: 11/791,008

(22) PCT Filed: Nov. 10, 2005

(86) PCT No.: PCT/EP2005/012047

§ 371 (c)(1),
(2), (4) Date: Oct. 17, 2007

(87) PCT Pub. No.: WO2006/053674

PCT Pub. Date: May 26, 2006

(65) Prior Publication Data

US 2008/0221320 A1    Sep. 11, 2008

(30) Foreign Application Priority Data

Nov. 19, 2004   (IT)  .......................... MI2004A2230

(51) Int. Cl.
*C07D 223/22*    (2006.01)

(52) U.S. Cl. ...................................... 540/587; 540/589
(58) Field of Classification Search ................. 540/587, 540/589

See application file for complete search history.

(56) References Cited

U.S. PATENT DOCUMENTS

| 5,049,637 A | 9/1991 | Copp et al. ................... 528/44 |
| 5,753,646 A | 5/1998 | Benes et al. |
| 6,384,217 B1 | 5/2002 | Atilio et al. |

FOREIGN PATENT DOCUMENTS

| EP | 1 127 877 A2 | 8/2001 |
| EP | 1127877 B1 | 6/2004 |
| GB | 1 310 120 | 3/1973 |
| WO | 02096881 A1 | 12/2002 |

OTHER PUBLICATIONS

Schill et al., "Ein neue Synthese von Vinblastin-Derivaten II" Tetrahedron, 43(16)3729-3745 (1987).
Benes et al., "Anticonvulsant and Sodium Channel-Blocking Properties of Novel 10,11-Dihydro-5H-dibenz[b,f]azepine-5-carboxamide Derivatives", J Med Chem 42:2582-2587 (1999).

*Primary Examiner*—Brenda L Coleman
(74) *Attorney, Agent, or Firm*—Porzio, Bromberg & Newman, P.C.

(57) ABSTRACT

A process for the preparation of 10,11-dihydro-10-hydroxy-5H-dibenz[b,f]azepine-5-carboxyamide by hydrolysis of 5-cyano-10,11-dihydro-10-hydroxy-5H-dibenz[b,f]azepine with peroxy compounds in alkali medium and in the presence of solvents.

9 Claims, No Drawings

PROCESS FOR THE PREPARATION OF 10,11-DIHYDRO-10-HYDROXY-5H-DIBENZ[B,F]AZEPINE-5-CARBOXYAMIDE

CROSS REFERENCE TO RELATED APPLICATION

This is a National Stage of International Application No. PCT/EP2005/012047, filed 10 Nov. 2005, which claims the benefit of Application No. MI2004A002230, filed in Italy on 19 Nov. 2004, the disclosures of which Applications are incorporated by reference herein.

The present invention relates to a novel process for the preparation of 10,11-dihydro-10-hydroxy-5H-dibenz[b,f]azepine-5-carboxyamide of formula 2, starting from 5-cyano-10,11-dihydro-10-hydroxy-5H-dibenz[b,f]azepine of formula 1, by hydrolysis of the CN group to $CONH_2$ group with peroxy compounds such as hydrogen peroxide, alkali or alkaline-earth metal perborates or persulfates, preferably with hydrogen peroxide, in alkali medium and in the presence of solvents, according to the scheme A shown hereinbelow:

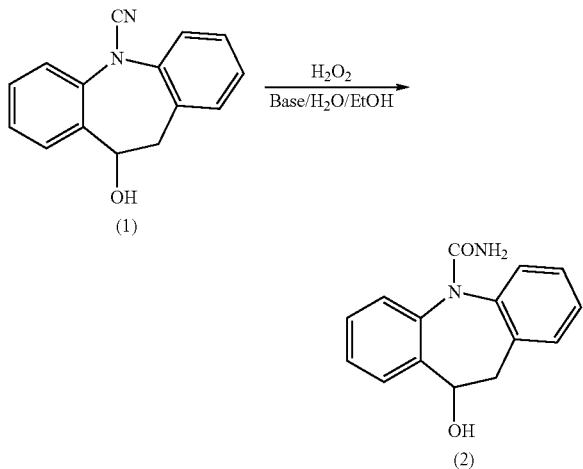

Nitrile 1 and the process for its preparation are disclosed in EP 1,127,877 and in corresponding U.S. Pat. No. 6,384,217 in the Applicant's name, which documents also report the hydrolysis to the corresponding carboxyamide 2. Said patents describe the hydrolysis of the cyano ketone but not that of the cyano alcohol. Compound 2 is an intermediate used in the synthesis of antiepileptic drugs: see, for instance, PCT WO 02/096881, U.S. Pat. No. 5,753,646 and the paper by J. Benes et al., *J. Med. Chem.* 1999. 42, 2582-2587.

The hydrolysis of nitrile 1 to amide under the conditions described in the patents cited above (sulfuric acid in acetic acid) mainly gives, however, the simultaneous dehydration of the —CHOH—$CH_2$— group with formation of a double bond. Conversely, it has now been found that the alcohol group is perfectly preserved when nitrile 1 is, as already mentioned, subjected to treatment with peroxy compounds in alkali medium, thereby obtaining 10,11-dihydro-10-hydroxy-5H-dibenz[b,f]azepine-5-carboxyamide of formula 2 in substantially quantitative yields.

According to a preferred embodiment of the invention, 5-cyano-10,11-dihydro-10-hydroxy-5H-dibenz[b,f]azepine 1 is suspended in a mixture of a $C_1$-$C_4$ alcohol (preferably ethanol), water and a base, such as an alkali or alkaline-earth metal hydroxide or carbonate, then slowly added with hydrogen peroxide or sodium perborate at temperature ranging from 0° C. to 50° C., and the mixture is reacted for some hours, until disappearance of the starting compound. The starting volume ratio of alcohol to water can range from 1:0.01 to 1:1. Alternatively, the reaction can be carried out starting without water, using an alkali alkoxide (preferably potassium tert-butoxide) as the base. As a further alternative, the reaction medium can be a phosphate buffered solution at pH 7.5 added with acetone, and the hydrolysis can be carried out by addition of potassium persulfate ("Oxone"). Finally, the reaction time can be minimized by use of microwaves.

The molar ratio of nitrile 1 to basic agent can range within wide limits, for example from 1:1 to 1:4; in any case, pH should be basic. The molar ratio of nitrile to active oxygen (independently of the source) is suitably kept between 1:1.5 and 1:4.

The following examples illustrate the process according to the invention.

EXAMPLE 1

200 g (1.45 moles) of $K_2CO_3$ dissolved in 200 ml of water are added with 700 ml of ethanol and 100 g (0.423 moles) of 5-cyano-10-hydroxy-10,11-dihydro-5H-dibenz[b,f]azepine. The suspension is cooled to 0° C. and 150 ml (166 g equivalent to 1.47 moles) of a 30% hydrogen peroxide solution are dropped therein in 1 hour at 0° C., keeping this temperature for one more hour. The mixture is then slowly warmed to 20° C., keeping this temperature for 3 hours. HPLC analysis shows the disappearance of the starting product; iodinated starch analysis shows that hydrogen peroxide is no longer present.

The lower aqueous phase is separated and discarded. The ethanol solution is evaporated to dryness under vacuum and the residual suspension is added with 500 ml of water, stirred at 20° C. for 2 hours, then filtered. The residue is washed with water and dried in a static dryer at 70° C. 95 g of compound 2 are obtained, with HPLC purity=95%.

30 g of compound 2 are dissolved under reflux in 80 ml of acetone+40 ml of water. The reaction is slowly cooled at room temperature, then to 0° C. for 2 hours and filtered, washing with 50 ml of a 1:1 acetone/water mixture, then with 50 ml of water. The residue is dried at 70° C. 23 g of 2 are obtained, with HPLC purity=99.1%.

Elemental analysis=

Calculated: C, 70.85%; H, 5.55%; N, 11.02%; O, 12.58%.

Found: C, 70.45%; H, 5.59%; N, 10.93%; O, 12.69%.

EXAMPLE 2

100 g (0.72 moles) of $K_2CO_3$ dissolved in 100 ml of water are added with 500 ml of ethanol and 100 g (0.423 moles) of 5-cyano-10-hydroxy-10,11-dihydro-5H-dibenz[b,f]azepine. The suspension is cooled at 0° C. and 80 ml (88.8 g equivalent to 0.78 moles) of a 30% hydrogen peroxide solution are dropped therein in 1 hour keeping this temperature for one more hour. The mixture is then slowly warmed to 20° C., keeping this temperature for 3 hours. HPLC analysis shows that the starting product is no longer present.

Ethanol is completely removed under vacuum and the residual suspension is added with 500 ml of water, stirred at 20° C. for 2 hours, then filtered. The residue is washed with water and dried in a static dryer at 70° C. 97 g of compound 2 are obtained, with HPLC purity=95.3%.

The product is crystallized following the procedure reported in Example 1 to obtain a product with quality comparable to that of the product obtained in Example 1.

EXAMPLE 3

60 g (0.435 moles) of $K_2CO_3$ dissolved in 120 ml of water are added with 300 ml of ethanol and 100 g (0.423 moles) of 5-cyano-10-hydroxy-10,11-dihydro-5H-dibenz[b,f]azepine. The suspension is cooled at 10° C. and 80 ml (88.8 g equivalent to 0.78 moles) of a 30% hydrogen peroxide solution are dropped therein in 1 hour, keeping the temperature at 10°-20° C. Then temperature is kept at 20°-25° C. for 3 hours. HPLC analysis shows that the starting product is no longer present.

Ethanol is completely removed under vacuum and the residual suspension is added with 150 ml of water, stirred at 20° C. for 2 hours, then filtered. The residue is washed with water and dried in a static dryer at 70° C. 98 g of compound 2 are obtained, with HPLC purity=94.5%.

The product is crystallized following the procedure reported in Example 1 to obtain a product with quality comparable to that of the product obtained in Example 1.

EXAMPLE 4

10 g (0.1 moles) of a 30% NaOH solution are dropped in 600 ml of isopropanol, then added with 100 g (0.423 moles) of 5-cyano-10-hydroxy-10,11-dihydro-5H-dibenz[b,f]azepine. The suspension is cooled at 0° C. and dropwise added with 80 ml (88.8 g equivalent to 0.78 moles) of a 30% hydrogen peroxide solution in 1 hour at 0° C., keeping this temperature for one more hour. The mixture is then slowly warmed to 20° C., keeping this temperature for 3 hours. HPLC analysis shows that the starting product is no longer present.

The mixture is cooled to 0° C. and stirred at this temperature for 2 hours, then filtered. The residue is washed with 100 ml of isopropanol at 0° C., then dried in a static dryer at 70° C. 80 g of product are obtained, with HPLC purity=97%.

This product is crystallized following the procedure reported in Example 1 to obtain a product with quality comparable to that of the product obtained in Example 1.

EXAMPLE 5

A mixture of 400 ml of ethanol and 400 ml of water is added with 100 g (0.423 moles) of 5-cyano-10-hydroxy-10, 11-dihydro-5H-dibenz[b,f]azepine. The suspension is heated to 50° C. and 100 g of sodium perborate (10% of active oxygen) are added thereto in small portions in 1 hour at this temperature, which is kept for one more hour.

HPLC analysis shows that the starting product is no longer present. Ethanol is completely distilled off under vacuum and the suspension is added with 300 ml of water, stirred at 20° C. for 2 hours, then filtered, washing with 100 ml of water. The residue is dried in a static dryer at 70° C. 100 g of compound 2 are obtained, with HPLC purity=94.3%.

The product is crystallized following the procedure reported in Example 1 to obtain a product with quality comparable to that of the product obtained in Example 1.

EXAMPLE 6

A suspension of 94 g (0.398 moles) of 5-cyano-10-hydroxy-10,11-dihydro-5H-dibenz[b,f]azepine in 500 ml of isopropanol is added with 142 g (12 mmol) of potassium tert-butoxide. The suspension is cooled at 0° C. and 300 ml of hydrogen peroxide (35% solution) are dropped therein in 1 hour at 0° C., keeping this temperature for one more hour, after which time iodinated starch analysis shows that hydrogen peroxide is no longer present, and HPLC analysis shows the disappearance of the starting product. Isopropanol is evaporated off under reduced pressure, pH is adjusted to approx. 3 with conc. HCl, and the mixture is extracted with ethyl acetate.

The organic phase is dried and concentrated to give 96.4 g of a crude which is recrystallized from isopropanol to afford 67.1 g of product, 66% yield.

EXAMPLE 7

A suspension of 5-cyano-10-hydroxy-10,11-dihydro-5H-dibenz[b,f]-azepine (8.5 mmol, 2 g) in 30 ml of a phosphate buffer solution pH=7.5 and acetone (10 ml) is added to a freshly prepared solution of oxone (26 g, 42.4 mmol) in 1:1 water/acetone (100 ml). During the addition, pH is kept basic by means of a 2N NaOH solution. The reaction mixture is refluxed for approx. 2 hours until total disappearance of the starting product (HPLC). The excess oxone is destroyed with a bisulfite solution, the mixture is extracted with ethyl acetate and dried over magnesium sulfate. The solvent is evaporated off under reduced pressure and the residue is crystallized to afford the desired amide (1.5 g, 67% yield).

EXAMPLE 8

5 g (21.18 mmol) of 5-cyano-10-hydroxy-10,11-dihydro-5H-dibenz-[b,f]azepine are dissolved in 20 ml of a water/ethanol 1:1 mixture. The resulting mixture is added with 13 g of sodium perborate (84.7 mmol) in small portions, then placed in a microwave oven (Prolabo Synthewave 402) and irradiated for 3 min. at 300 Watt.

The reaction mixture is cooled, ethanol is evaporated off under reduced pressure and the resulting liquid is extracted with ethyl acetate (3×50 ml). The extracted organic phase is dried over sodium sulfate and concentrated. 3.7 g (69% yield) are obtained.

The invention claimed is:
1. A process for the preparation of 10,11-dihydro-10-hydroxy-5H-dibenz[b,f]azepine-5-carboxyamide of formula 2

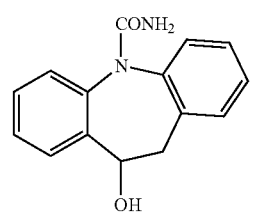

(2)

characterized in that the nitrile group of 5-cyano-10,11-dihydro-10-hydroxy-5H-dibenz[b,f]azepine of formula 1

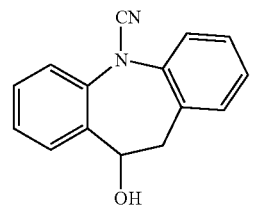

(1)

is subjected to hydrolysis with peroxy compounds in alkali medium and in the presence of solvents.

2. A process as claimed in claim 1, characterized in that the peroxy compounds are selected from hydrogen peroxide or alkali or alkaline-earth metal perborates or persulfates.

3. A process as claimed in claim 2, characterized in that the peroxy compound is hydrogen peroxide.

4. A process as claimed in claim 1, characterized in that the molar ratio of 5-cyano-10,11-dihydro-10-hydroxy-5H-dibenz[b,f]azepine to peroxy compound ranges from 1:1.5 to 1:4.

5. A process as claimed in claim 1, characterized in that the alkali medium is selected from alkali or alkaline-earth metal hydroxides, alkoxides or carbonates.

6. A process as claimed in claim 1, characterized in that the molar ratio of 5-cyano-10,11-dihydro-10-hydroxy-5H-dibenz[b,f]azepine to base ranges from 1:1 to 1:4.

7. A process as claimed in claim 1, characterized in that the solvents are selected from lower alcohols.

8. A process as claimed in claim 7, characterized in that the solvent is ethanol or isopropanol.

9. A process as claimed in claim 1, characterized in that the reaction is carried out in the presence of microwaves.

\* \* \* \* \*